(12) United States Patent
Mase et al.

(10) Patent No.: US 7,460,905 B2
(45) Date of Patent: Dec. 2, 2008

(54) SYSTEM FOR DISPLAYING VITAL SIGN DATA

(75) Inventors: Ryuzo Mase, Tokyo (JP); Xiangji Li, Tokyo (JP); Kaoru Imajo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 11/330,102

(22) Filed: Jan. 12, 2006

(65) Prior Publication Data

US 2006/0161072 A1  Jul. 20, 2006

(30) Foreign Application Priority Data

Jan. 14, 2005  (JP)  ............................ P2005-007120

(51) Int. Cl.
*A61B 5/04* (2006.01)
(52) U.S. Cl. ...................................... 600/544
(58) Field of Classification Search ................ 600/300, 600/301, 544, 545; 128/920–925
See application file for complete search history.

(56) References Cited

U.S. PATENT DOCUMENTS

| | | | | |
|---|---|---|---|---|
| 4,557,270 A * | 12/1985 | John | .......................... | 600/544 |
| 4,800,895 A * | 1/1989 | Moberg et al. | .............. | 600/544 |
| 5,262,944 A | 11/1993 | Weisner et al. | | |
| 5,365,936 A * | 11/1994 | Kyu | ............................. | 600/523 |
| 5,420,298 A * | 5/1995 | Edwards et al. | ............. | 548/556 |
| 5,544,649 A * | 8/1996 | David et al. | .................. | 600/301 |
| 5,564,433 A * | 10/1996 | Thornton | .................... | 600/544 |
| 5,720,298 A * | 2/1998 | Papakostopoulos | .......... | 600/300 |
| 5,798,798 A * | 8/1998 | Rector et al. | ................. | 348/476 |
| 6,224,549 B1 * | 5/2001 | Drongelen | .................... | 600/300 |
| 6,473,639 B1 * | 10/2002 | Fischell et al. | .............. | 600/544 |
| 6,511,424 B1 * | 1/2003 | Moore-Ede et al. | ......... | 600/300 |
| 7,038,588 B2 * | 5/2006 | Boone et al. | ............. | 340/573.1 |
| 2003/0055356 A1 | 3/2003 | Nonaka | | |
| 2005/0080828 A1* | 4/2005 | Johnson | ....................... | 708/160 |
| 2005/0177312 A1* | 8/2005 | Guerrant et al. | ................ | 702/19 |

FOREIGN PATENT DOCUMENTS

| | | |
|---|---|---|
| JP | 7-163527 A | 6/1995 |
| JP | 10-504144 A | 4/1998 |
| JP | 2002-541891 A | 12/2002 |
| JP | 2003-79591 A | 3/2003 |
| WO | WO 95/30304 A | 11/1995 |

* cited by examiner

*Primary Examiner*—Charles A. Marmor, II
*Assistant Examiner*—Navin Natnithithadha
(74) *Attorney, Agent, or Firm*—Sughrue Mion, PLLC

(57) ABSTRACT

Each of a plurality of electroencephalographs is adapted to measure electroencephalograms of a patient and to be connected to a communication network. Each of the electroencephalographs is operable to analyze the electroencephalograms to generate electroencephalogram information. Each of a plurality of cameras is adapted to monitor a state that the patient is subjected to the electroencephalogram measurement to transmit the monitored state as image information to associated one of the electroencephalographs. A central control monitor is connected to the communication network and operable to simultaneously displaying the electroencephalogram information and a part of the image information which are transmitted from each of the electroencephalographs via the communication network.

9 Claims, 4 Drawing Sheets

SYSTEM FOR DISPLAYING VITAL SIGN DATA

BACKGROUND OF THE INVENTION

The invention relates to a system for displaying vital sign data. More particularly, the invention relates to a system for simultaneously measuring and monitoring electroencephalograms of a number of patients by use of a plurality of electroencephalographs.

Conventionally, an electroencephalograph has successively displayed, on a display section, an electroencephalogram derived from electrodes by way of a junction box, analysis data (a frequency spectrum) obtained through analysis of the electroencephalogram, or the like, and recorded the same in a recorder; or stored the same in a storage. In addition, there have hitherto been practiced long-hour measurement; application of an auditory or a photo stimulation to the patient; or capture of an image of a patient by a video camera with permission from the patient for the purpose of monitoring the state of the patient. The thus-obtained image is displayed on a display of the electroencephalograph in conjunction with electroencephalographic waveforms and the analysis data.

Japanese Patent Publication No. 2002-541891A discloses a technique of displaying an electroencephalographic waveform on the upper left portion of the screen, and an image showing a state of a patient captured by a video camera on the lower right portion, thereby displaying these on a single screen.

Japanese Patent Publication No. 2003-79591A discloses a method of displaying on a single screen an electroencephalographic waveform per se and a DSA (density spectral array) obtained through analysis of the electroencephalogram.

Meanwhile, a DSA display method is such a display method that an electroencephalogram is subjected to FFT (fast Fourier transform); and a bar-shaped image is displayed at a predetermined time interval while the density of dots (black dots) of the bar is changed or the color of the same is changed in accordance with the amplitude of the electroencephalogram obtained after the FFT analysis, wherein the Y axis represents a frequency, and the X axis represents time.

As described above, electroencephalography is usually performed with use of a single electroencephalograph per patient to be measured, while a technician is on standby at the electroencephalograph. During measurement, the technician must monitor the state of electroencephalograms displayed on a screen of the electroencephalograph and an image of the patient displayed on a screen, thereby maintaining such a condition that, in the event of detachment of electrodes attached on the patient, occurrence of an abnormal condition to the patient, or the like, the technician can respond immediately.

However, in an epilepsy-specialized hospital, or the like, electroencephalograms of a plurality of patients must be measured continuously over several hours, over several days, or, in a case of long-term measurement, over one week under patient-specific conditions. In such a case, a single technician is to be assigned for a single electroencephalograph. However, since an abnormal condition rarely occurs in a patient, provision of a single technician for a single electroencephalograph over several days to one week has been unrealistic. To this end, for the purpose of reducing the number of technicians, the following method has been proposed.

Namely, as an easy and convenient method for solving the problem, there has been proposed a method of displaying and monitoring only video signals output from respective video cameras on a single monitor in a centralized manner by screen splitting so as to monitor only measurement states of patients. In this case, since only states of the patients are monitored in the form of video images without monitoring electroencephalograms, there has arisen a problem that insufficient information poses difficulty in making appropriate response.

Alternatively, as another method, displaying electroencephalograms output from electroencephalographs and video signals output from video cameras on a central control monitor is also conceivable. However, electroencephalograms output from a single electroencephalograph number from, even in a minimum volume, 32 channels to, in a case of a large volume, as many as 250 channels. Accordingly, connection of a plurality of electroencephalographs to a single central control monitor, to thus perform display, has encountered technical difficulty in implementation because of problems in signal sampling, shortage in data transfer rate or processing data rate of a communication network, and like problems.

SUMMARY OF THE INVENTION

It is therefore an object of the invention to provide a system for measuring electroencephalograms of a plurality of patients under different conditions over a long period of time, while enabling a reduction in the number of technicians who monitor states of patients, and analysis data pertaining to electroencephalograms.

It is also an object of the invention to provide a system for displaying vital sign data, which enables accurate ascertainment as to in which patient, among a plurality of patients, an abnormal condition has occurred, by a small number of technicians.

In order to achieve the above object, according to the invention, there is provided a system for displaying vital sign data, comprising:

a plurality of electroencephalographs, each of which is adapted to measure electroencephalograms of a patient and to be connected to a communication network, each of the electroencephalographs being operable to analyze the electroencephalograms to generate electroencephalogram information;

a plurality of cameras, each of which is adapted to monitor a state that the patient is subjected to the electroencephalogram measurement to transmit the monitored state as image information to associated one of the electroencephalographs; and a central control monitor, connected to the communication network and operable to simultaneously displaying, in a first display region, the electroencephalogram information and a part of the image information which are transmitted from each of the electroencephalographs via the communication network.

Each of the electroencephalographs may comprise a storage adapted to store the electroencephalograms and the image information. The central control monitor may be operable to receive a request including information indicative of a time point, and to display, in a second display region, the electroencephalograms and the image information of at least the time point which are read out from the storage in one of the electroencephalographs.

The central control monitor may be operable to issue an alarm when a prescribed event is detected in at least one of the electroencephalographs.

The electroencephalogram information may be a density spectral array of the electroencephalograms.

The image information may be obtained at a first frame rate and the part of the image information may be extracted at a second frame rate which is lower than the first frame rate.

With the above configurations, the measurement states of a plurality of patients can be monitored accurately by a smaller number of technicians.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE EMBODIMENTS

Embodiments of the invention will be described below in detail with reference to the accompanying drawings.

Figure 1:
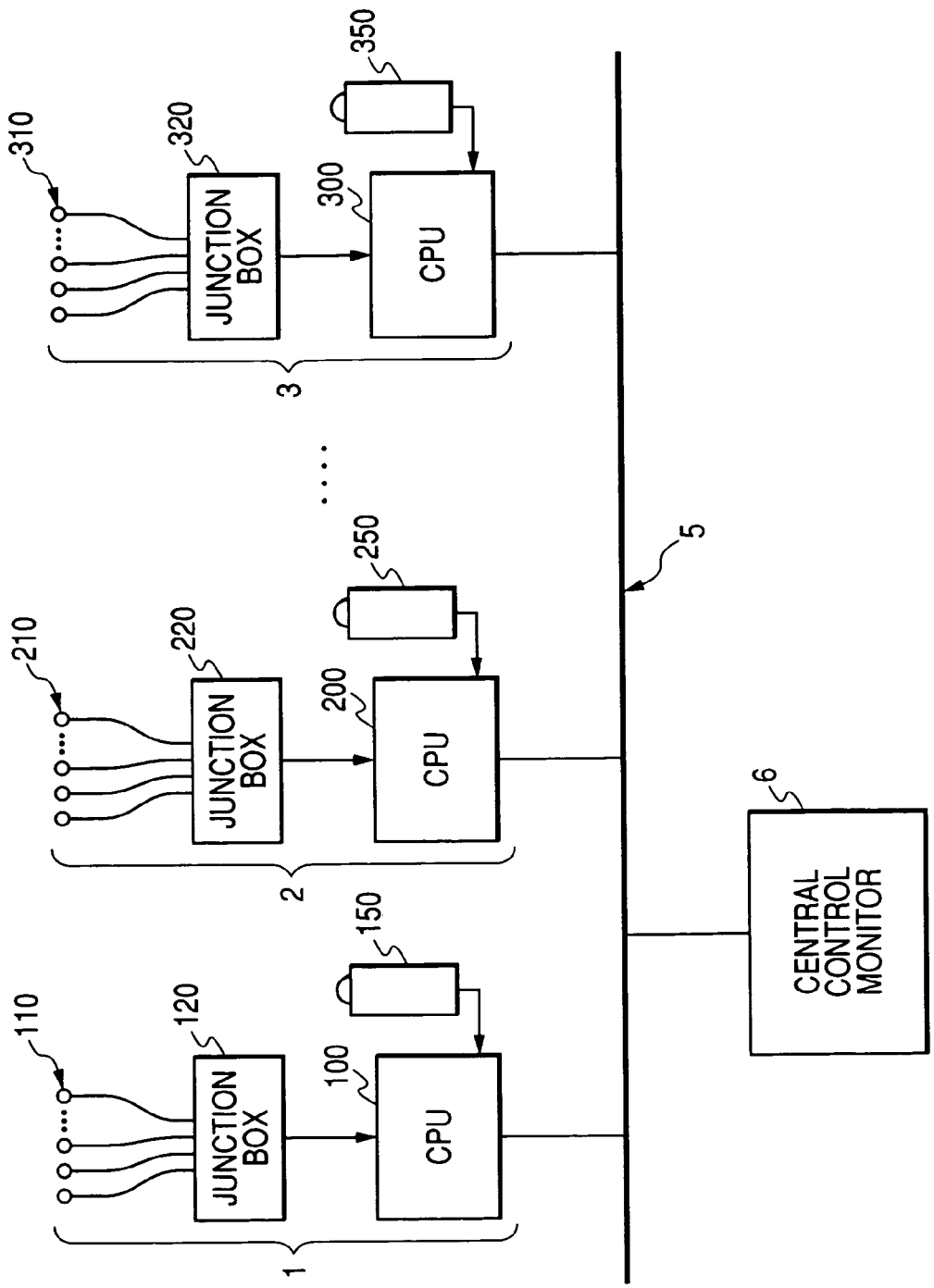
FIG. 1 is a block diagram showing a system for displaying vital sign data, according to one embodiment of the invention.

As shown in FIG. 1, in a system for displaying vital sign data according to one embodiment, a plurality of electroencephalographs 1, 2, 3 are connected in a number within a range that satisfies a condition that enables connection to a communication network 5. A central control monitor 6 is connected to the communication network 5.

In the system configured as above, electrodes 110 are respectively placed and connected on an unillustrated living body. The number of the electrodes is usually 22. However, in a case of monitoring a symptom of epilepsy, or the like, more than 22 electrodes are often placed in a connecting manner.

Figure 2:
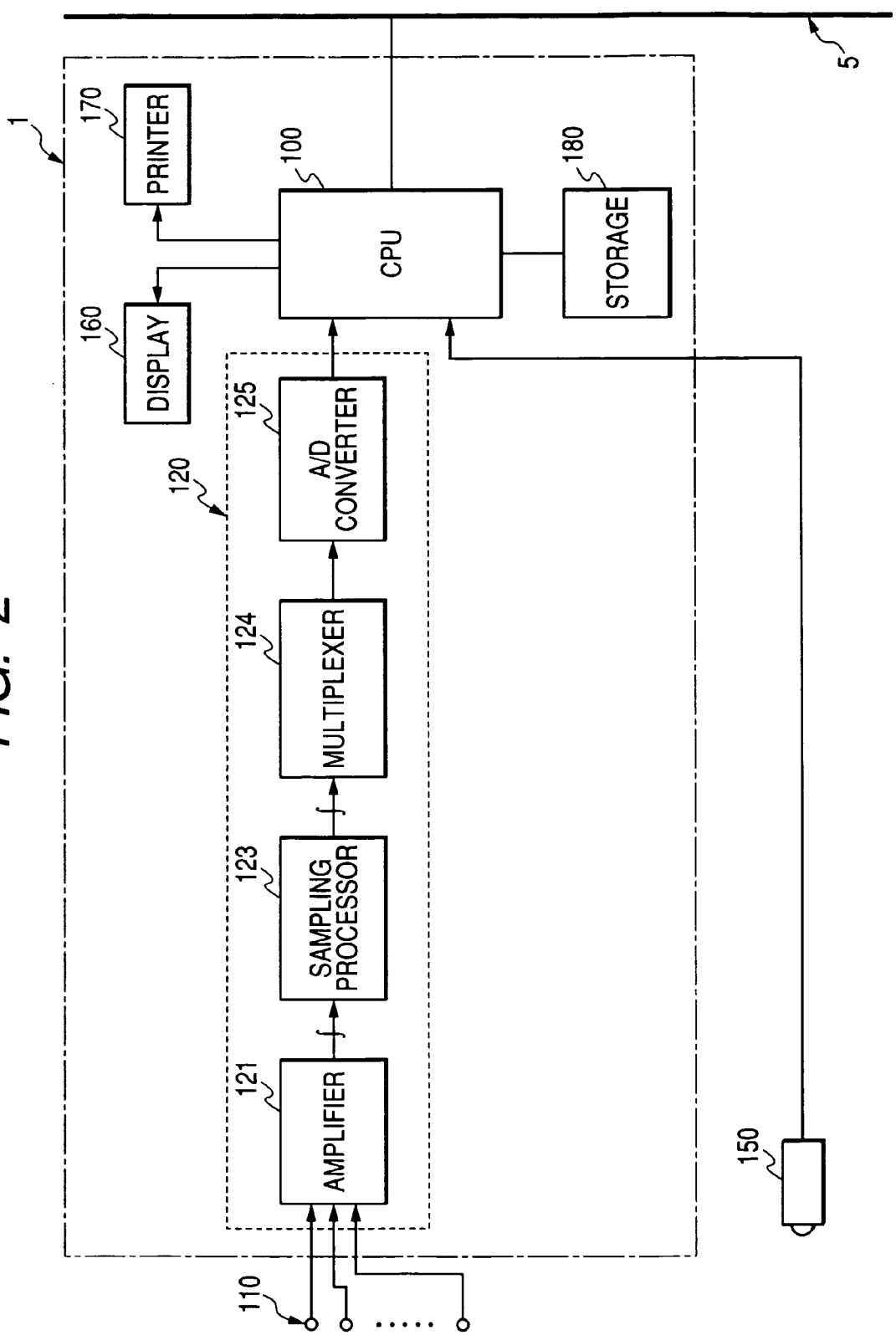
FIG. 2 is a block diagram showing an electroencephalograph in the system.

As shown in FIG. 2, leads of the electrodes 110 are connected to a junction box 120, and guided to an amplifier 121. Output signals from the amplifier 121 are subjected to sampling processing by a sampling processor 123, and input into a multiplexer 124. Thus far, the output signals are processed by way of a plurality of signal lines. However, a signal having been synthesized by the multiplexer 124 is output to a single signal line. The output signal obtained in the multiplexer 124 is transferred to an A/D converter 125, to thus be converted into a digital signal, and input into a CPU 100.

An output of an image of a patient captured by a camera 150 is input into the CPU 100. Subsequently, signal processing and control are performed, such as displaying an image and an electroencephalographic waveform on a display 160, outputting the electroencephalographic waveform to a printer 170, and further storing the same into a storage 180. Depending on a type of an electroencephalograph, there are some cases where signal processing, such as DSA processing, is also performed in the CPU 100, followed by storage into the storage 180.

In this embodiment, the CPU 100 of the electroencephalograph 1 has a function of outputting an image of a patient and DSA analysis data sets to the communication network 5 by way of an unillustrated interface. Each of the electroencephalographs 2 and 3 has the same functions. Electroencephalographs in a number satisfying a condition that enables connection to a network are connected to the communication network 5.

Figure 3:
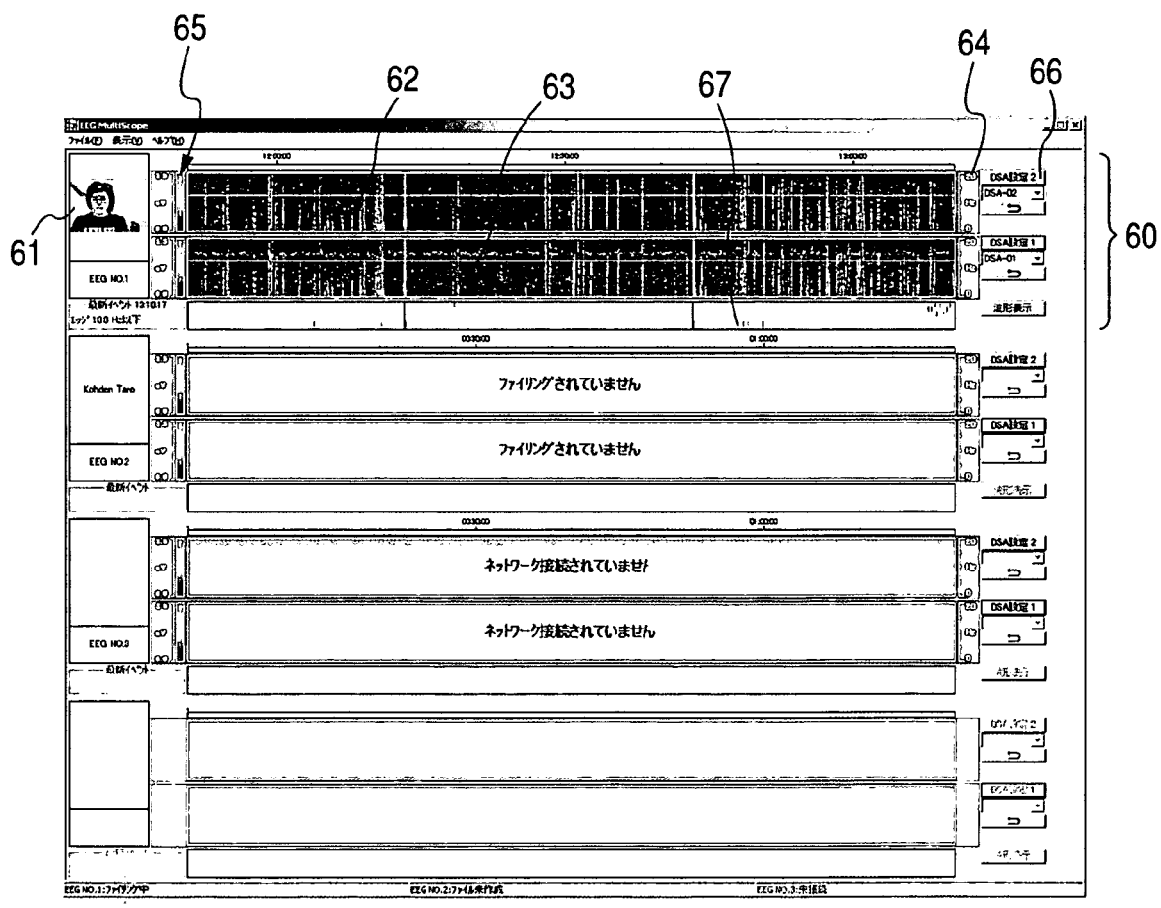
FIG. 3 shows a first example screen displayed on a display of a central control monitor in the system.

The central control monitor 6 to be connected to the communication network 5 comprises a CPU, a display, a speaker, a printer, and so on although they are not specifically illustrated. FIG. 3 illustrates an example screen display on a display of the central control monitor 6, showing data pertaining to four patients. Assuming that reference numeral 60 denotes a display area for a single person, and that data pertaining toga patient being measured by the electroencephalograph 1 are displayed thereon, descriptions are provided of the contents displayed thereon.

In FIG. 3, a current state of the patient is displayed in the form of image on the left of the display screen. More specifically, an image of the patient, which is obtained by processing video signals captured by the camera 150 in the CPU 100 of the electroencephalograph 1 and which is transmitted to the communication network 5, is displayed on a display section 61. Since the image data are of a large volume, in a case where all of the image data are transmitted to the communication network 5, a transfer rate of the communication network 5 cannot keep pace therewith, thereby lapsing into an overflow state.

Therefore, in this embodiment, image data output from the camera 150 are transmitted to the communication network 5 after a frame rate thereof has been lowered by the CPU 100 of the electroencephalograph 1. The central control monitor 6 captures the image data, and displays the same as a current state of the patient while updating the same at a given time interval. Reference numerals 62 and 63 respectively denote display sections for DSA analysis data sets pertaining to an electroencephalogram of the patient measured with the electroencephalograph 1. The display sections 62 and 63 for the DSA analysis data perform display in two channels for allowing, e.g., comparison between a state of the right side of the patient's head and that of the left side of the patient's head.

Rather than display on the basis of DSA, an electroencephalographic waveform per se is desirably displayed. However, displaying electroencephalographic data ranging over a number of channels involves problems; e.g., that a transfer rate of the communication network 5 cannot keep pace therewith. Even under the assumption that transfer is successful, the screen of the central control monitor 6 whose object lies in monitoring images and electroencephalographic data pertaining to a number of patients becomes complicated, which is not preferable.

The display sections 62 and 63 for DSA analysis data perform display as follows. First, the DSA analysis data are calculated by the CPU 100 of the electroencephalograph 1. Electroencephalographic waveforms of 5-second intervals which overlap by 2.5 seconds are subjected to FFT analysis, and a single set of DSA analysis data is output to the communication network 5 every 2.5 seconds. The central control monitor 6 displays the DSA analysis data on the display sections 62 and 63. The DSA analysis data are displayed such that the right end of the X-axis represents the present, and the left thereof represents the past. Display of the DSA analysis data depends on resolution of a screen of a display section employed in the central control monitor 6, and on a time range to be displayed. For instance, when the time range to be displayed is set to a long time, a single dot displayed on a temporal axis corresponds to several tens of seconds. Since a single set of the DSA analysis data is obtained every 2.5 seconds, several sets of the DSA analysis data are represented by a single dot. However, in this case, the DSA analysis data are represented in the form of an average value of several sets of data or a maximum value of several data sets. The average value or the maximum value is calculated at predetermined frequencies.

Other electroencephalographs connected to the communication network 5 are set in the same manner. The central control monitor 6 captures DSA analysis data from these electroencephalographs by way of the communication network 5 and displays the same on the screen. The Y-axis represents frequency components of the FFT analysis, and the frequency values are displayed on a display section 64. In this case, intensities of the respective frequencies can be displayed by use of color-coding. A color legend is indicated on the left corners of the display sections 62 and 63 for the DSA data; and can be set so that, e.g., blue represents a low intensity and red represents a high intensity.

To the right of the display section 64 for the frequency of the DSA analysis data, there is disposed a DSA setting window 66 for instructing and displaying a measurement portion of a patient to be output from the electroencephalograph 1. Below the display sections 62 and 63 for the DSA analysis data in the display area 60 for a single patient, events having occurred in the past are displayed on a display section 67 in accordance with the time axis of the displayed DSA analysis data.

Next, the display sections 62 and 63 for the DSA analysis data are monitored. When a portion of concern or a case which appears to be a specific event is found, a cursor is moved to the portion to thus designate the portion, whereby an electroencephalographic waveform of the portion; that is, a time point corresponding thereto, can be displayed. More specifically, when, e.g., a cursor is moved, by use of a mouse, or the like, to an arbitrary portion on the DSA analysis data pertaining to the patient 1 on display and double-clicking is performed, the central control monitor 6 transfers to the electroencephalograph 1 an instruction about the time by way of the communication network 5.

Figure 4:
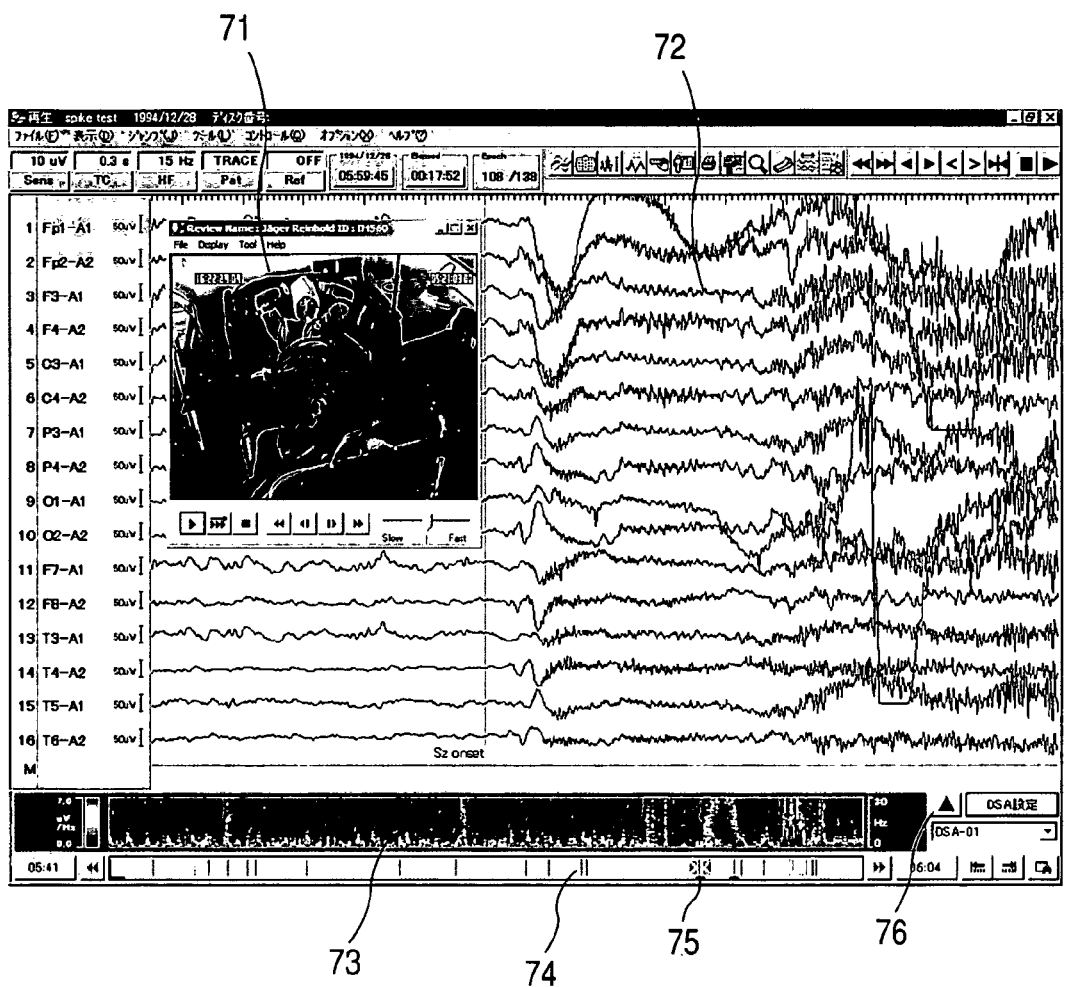
FIG. 4 shows a second example screen displayed on a display of a central control monitor in the system.

On the basis of the instruction, the electroencephalograph 1 reads image data in accordance with the thus-designated time and electroencephalographic waveforms in the vicinity of the designated time from the storage 180 in which all the measured values and measurement history are stored, and outputs the same to the communication network 5. Then, the central control monitor 6 displays a screen as illustrated in FIG. 4. An image of the designated time point is displayed on a display section 71. In addition, electroencephalograms in the vicinity of the designated time point are displayed on a display section 72. On a display section 73 at the lower section of the screen, DSA analysis data are displayed with the latest measurement time point at the right end, in such a manner that continued data from the DSA analysis data having been displayed on the screen precede to switching to the current screen display.

In FIG. 4, reference numeral 74 denotes a display section for an event. Similar to the display of the DSA analysis data, an event continued from an event having been displayed on the preceding screen is displayed also on this display section 74. A display section 75 indicates a time point of the image and of the electroencephalographic waveforms displayed above the display section 75. In addition, when a task is selected among tasks displayed on an unillustrated task bar of the OS, the screen display returns to the screen display illustrated in FIG. 3 where four patients are displayed on the screen.

At a time point of occurrence of an event, an event mark is displayed on the display section 67. Examples of cases where an event occurs in relation to an electroencephalograph are as follows. More specifically, the electroencephalograph outputs an event-occurrence signal when an event button on the electroencephalograph is pressed; when the electroencephalograph analyzes an electroencephalogram, thereby determining an occurrence of a seizure or an occurrence of a predetermined event, or when a patient presses a "CALL" button.

When the central control monitor 6 receives the event-occurrence signal, a window notifying of occurrence of the event is opened. The window blinks and/or sounds a beep, thereby reporting from which patient's electroencephalograph the event signal has originated. Meanwhile, with regard to the sound, when a voice or a sound tone which allows identification of the electroencephalograph or a type of an event is set for each patient; that is, for each electroencephalograph, identification of the event is facilitated.

Hithertofore, as a preferred embodiment of the invention, display of DSA data as electroencephalograph analysis data has been described. However, the electroencephalograph analysis data are not limited thereto, and, e.g., amplitude trend data pertaining to electroencephalograph analysis data can be employed. The embodiment can be modified in various manners within the scope of the invention.

For example, each of the images shown in FIGS. 3 and 4 may occupy at least a part of the display screen in the central control monitor 6. Further, each of the images shown in FIGS. 3 and 4 may be presented in different regions provided in at least one display screen in the central control monitor 6.

What is claimed is:

1. A system for displaying vital sign data, comprising:
    a plurality of electroencephalographs, each of which is adapted to measure electroencephalograms of a patient and to be connected to a communication network, each of the electroencephalographs being operable to generate electroencephalogram information which is information obtained by successively analyzing a plurality of electroencephalograms of uniform prescribed time intervals;
    a plurality of cameras, each of which is adapted to monitor a state of the patient subjected to the electroencephalogram measurement, and to transmit the monitored state as image information to an associated one of the electroencephalographs; and
    a central control monitor, connected to the communication network and operable to simultaneously display for a plurality of patients, in a first display region, the electroencephalogram information and a part of the image information which are transmitted from each of the electroencephalogram graphs via the communication network.

2. The system as set forth in claim 1, wherein:
    each of the electroencephalographs comprises a storage adapted to store the electroencephalograms and the image information; and
    the central control monitor is operable to receive a request including information indicative of a time point, and to display, in a second display region, the electroencephalograms and the image information of at least the time point which are read out from the storage in one of the electroencephalographs.

3. The system as set forth in claim 1, wherein the central control monitor is operable to issue an alarm when a prescribed event is detected in at least one of the electroencephalographs.

4. The system as set forth in claim 1, wherein the image information is obtained at a first frame rate and the part of the image information is extracted at a second frame rate which is lower than the first frame rate.

5. The system as set forth in claim 1, wherein the electroencephalogram information is obtained by subjecting the electroencephalograms to frequency analysis.

6. The system as set forth in claim 5, herein the frequency analysis is fast Fourier transform.

7. The system as set forth in claim 6, wherein the electroencephalogram information is a density spectral array of the electroencephalograms.

8. The system as set forth in claim 1, wherein the electroencephalogram information has a smaller data amount than that of the electroencephalograms.

9. The system as set forth in claim 1, wherein:
the electroencephalogram information has at least one channel, the number of said at least one channel being less than the number of channels of the electroencephalograms; and
the electroencephalogram information has an appearance different from that of the electroencephalograms.

* * * * *